US009103650B2

(12) United States Patent
Suehira et al.

(10) Patent No.: US 9,103,650 B2
(45) Date of Patent: Aug. 11, 2015

(54) OPTICAL TOMOGRAPHIC IMAGE GENERATION METHOD AND OPTICAL TOMOGRAPHIC IMAGE GENERATION APPARATUS

(75) Inventors: Nobuhito Suehira, Kawasaki (JP); Mitsuro Sugita, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 411 days.

(21) Appl. No.: 12/893,393

(22) Filed: Sep. 29, 2010

(65) Prior Publication Data

US 2011/0096333 A1 Apr. 28, 2011

(30) Foreign Application Priority Data

Oct. 23, 2009 (JP) ................................. 2009-244696

(51) Int. Cl.
*G01B 9/02* (2006.01)
*A61B 3/10* (2006.01)
*A61B 5/00* (2006.01)

(52) U.S. Cl.
CPC ............ *G01B 9/02087* (2013.01); *A61B 3/102* (2013.01); *A61B 5/0066* (2013.01); *A61B 5/0073* (2013.01); *A61B 5/7257* (2013.01); *G01B 9/02044* (2013.01); *G01B 9/02083* (2013.01); *G01B 9/02091* (2013.01); *A61B 5/7203* (2013.01)

(58) Field of Classification Search
CPC ........... G01B 9/02091; G01B 9/02004; G01B 9/02044
USPC ................................................ 356/497, 479
See application file for complete search history.

(56) References Cited

U.S. PATENT DOCUMENTS

| 5,321,501 | A  | * | 6/1994 | Swanson et al. ............... 356/479 |
| 7,936,462 | B2 |   | 5/2011 | Jiang et al. |
| 2002/0094114 | A1 | * | 7/2002 | Ogino ........................... 382/128 |
| 2003/0103212 | A1 | * | 6/2003 | Westphal et al. ............. 356/479 |
| 2007/0222946 | A1 |   | 9/2007 | Fukuma et al. |
| 2008/0175465 | A1 | * | 7/2008 | Jiang et al. .................... 382/131 |
| 2008/0234972 | A1 |   | 9/2008 | Tsukada et al. |

(Continued)

FOREIGN PATENT DOCUMENTS

JP 2008-039651 A 2/2008
JP 2008-142443 A 6/2008

(Continued)

OTHER PUBLICATIONS

Grant R. Fowles, Introduction to Modern Optics, 1975, Dover Publications, 2nd Ed., pp. 68-73.*

(Continued)

*Primary Examiner* — Jonathan Hansen
(74) *Attorney, Agent, or Firm* — Fitzpatrick, Cella, Harper & Scinto

(57) ABSTRACT

Provided is a method for easily improving image quality in an optical tomographic imaging apparatus. An optical tomographic image generation method of generating a tomographic image of an object includes: acquiring a signal; performing Fourier transform; and obtaining the tomographic image. The optical tomographic image generation method further includes one of the steps of combining a plurality of the signals acquired within a predetermined time and combining a plurality of the signals acquired within a predetermined time after performed the Fourier transform thereon.

29 Claims, 6 Drawing Sheets

(56) References Cited

U.S. PATENT DOCUMENTS

| | | | |
|---|---|---|---|
| 2008/0285913 A1* | 11/2008 | Yang et al. .................... 385/24 |
| 2010/0110171 A1 | 5/2010 | Satake |
| 2010/0166293 A1 | 7/2010 | Sugita et al. |
| 2010/0181462 A1 | 7/2010 | Sugita |
| 2010/0226553 A1 | 9/2010 | Suehira |
| 2010/0226554 A1 | 9/2010 | Suehira |
| 2011/0058175 A1 | 3/2011 | Suehira |
| 2011/0098560 A1 | 4/2011 | Suehira et al. |

FOREIGN PATENT DOCUMENTS

| | | | |
|---|---|---|---|
| JP | 2008-237238 A | 10/2008 |
| JP | 2010-110392 A | 5/2010 |
| WO | 2008/052793 A1 | 5/2008 |
| WO | 2009-034704 A1 | 3/2009 |

OTHER PUBLICATIONS

Office Action dated Dec. 7, 2011, in Japanese Application No. 2009-244696.

Search Report for corresponding European Appln. No. 10188408.8 dated Feb. 17, 2011.

Jan. 18, 2013 Chinese Official Action in Chinese Patent Appln. No. 201010515596.0.

* cited by examiner

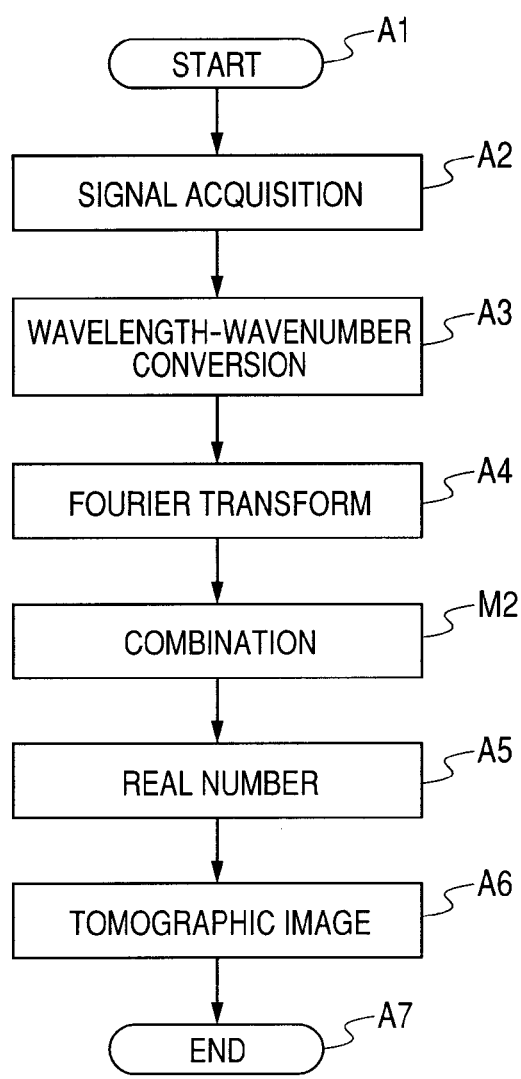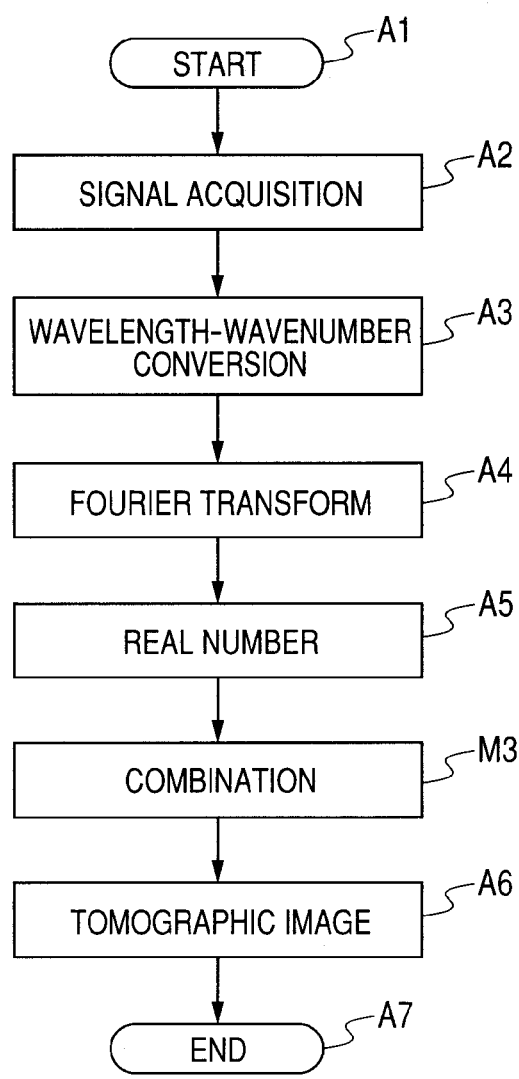

OPTICAL TOMOGRAPHIC IMAGE GENERATION METHOD AND OPTICAL TOMOGRAPHIC IMAGE GENERATION APPARATUS

BACKGROUND OF THE INVENTION

1. Field of the Invention

The present invention relates to an optical tomographic image generation method and an optical tomographic image generation apparatus that are used for generating a tomographic image of an object.

2. Description of the Related Art

An imaging apparatus using optical coherence tomography (OCT) in which interference of low coherent light is utilized (hereinafter, also referred to as OCT apparatus) is now put into practical use. This imaging apparatus is capable of acquiring a tomographic image at a depth resolution of several micrometers, which leads to high-resolution imaging of a tomographic image of an object.

Japanese Patent Application Laid-Open No. 2008-237238 discloses an optical image measurement device that is intended to improve image quality of an image to be formed. This device forms multiple tomographic images of an eye fundus and stores the formed images. Then, one of the tomographic images and a tomographic image adjacent thereto are used for an arithmetic operation, to thereby form a new tomographic image. As a result, the image quality of the formed image can be improved.

In Japanese Patent Application Laid-Open No. 2008-237238 described above, the image quality is improved to some extent, but is not improved sufficiently. Particularly in a case where the object moves, its position varies between the tomographic images, which raises a risk that signal waveforms are rounded.

Therefore, further improvement in image quality is demanded.

SUMMARY OF THE INVENTION

The present invention has been made to solve the above-mentioned problem, and it is therefore an object of the present invention to achieve further improvement in image quality. Another object of the present invention is to achieve improvement in image quality even when an object moves, by suppressing influence of the movement of the object.

According to the present invention, there is provided an optical tomographic image generation method of generating a tomographic image of an object, including the steps of: acquiring a signal; performing Fourier transform; and obtaining a tomographic image, in which the optical tomographic image generation method further includes one of the steps of combining a plurality of the signals acquired within a predetermined time and combining a plurality of the signals acquired within a predetermined time after performing the Fourier transform thereon.

According to the present invention, there is also provided an optical tomographic image generation apparatus for splitting a light from a light source into a measurement light and a reference light, guiding the measurement light to an object through a measurement light path, and guiding the reference light to a reference mirror through a reference light path, to thereby generate a tomographic image of the object by using a return light, which is the measurement light reflected or scattered by the object, the reference light reflected on the reference mirror, and a combined light obtained by combining the return light and the reference light, the optical tomographic image generation apparatus including a unit for scanning the object and a unit for controlling imaging timing and further includes a unit for combining signals acquired within a predetermined time.

According to the present invention, improvement in image quality is achieved by combining the plurality of the signals acquired within the predetermined time or combining signals obtained after performing the Fourier transform on the plurality of the signals.

Further features of the present invention will become apparent from the following description of exemplary embodiments with reference to the attached drawings.

BRIEF DESCRIPTION OF THE DRAWINGS

FIGS. 5A and 5B are explanatory diagrams illustrating signal processing steps according to the second embodiment of the present invention.

DESCRIPTION OF THE EMBODIMENTS

Preferred embodiments of the present invention will now be described in detail in accordance with the accompanying drawings.

Figure 1:
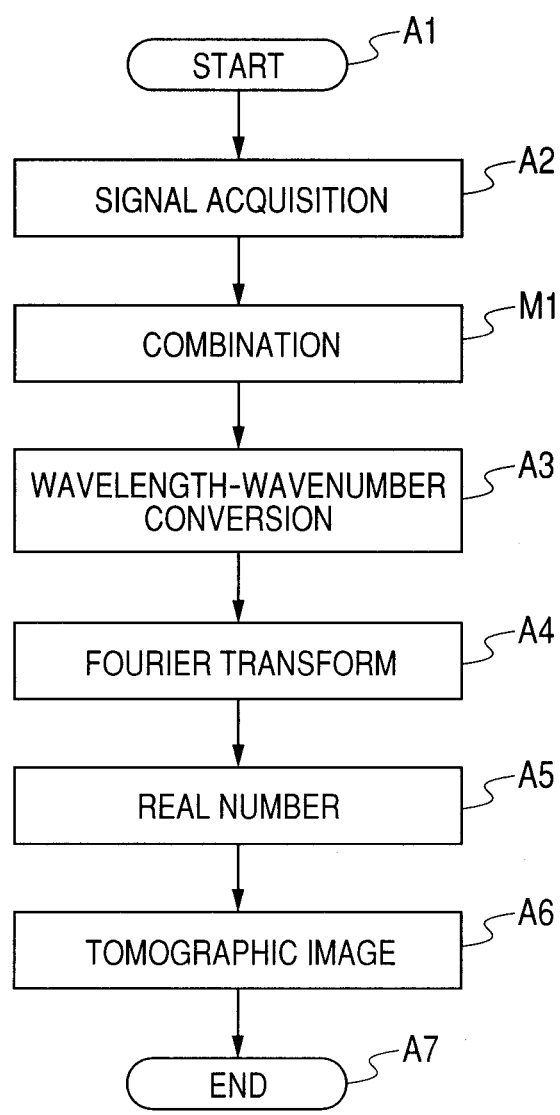
FIG. 1 is an explanatory diagram illustrating signal processing steps according to a first embodiment of the present invention.

According to the present invention, there is provided an optical tomographic image generation method of generating a tomographic image of an object, including the steps of: acquiring a signal; performing Fourier transform; and obtaining the tomographic image, in which the optical tomographic image generation method further includes one of the steps of combining a plurality of the signals acquired within a predetermined time and combining a plurality of the signals acquired within a predetermined time after performing the Fourier transform thereon. FIG. 1 illustrates a case where the optical tomographic image generation method includes the step of combining a plurality of the signals acquired within a predetermined time.

EMBODIMENTS

First Embodiment

Next, a first embodiment of the present invention is described. In this embodiment, an imaging apparatus using a Michelson interferometer is employed for generating a tomographic image, but the imaging apparatus employable for the present invention is not limited thereto. Further, signal processing of this embodiment is characterized in combining multiple signals after the signals are acquired.

Michelson Interferometer

Figure 2:
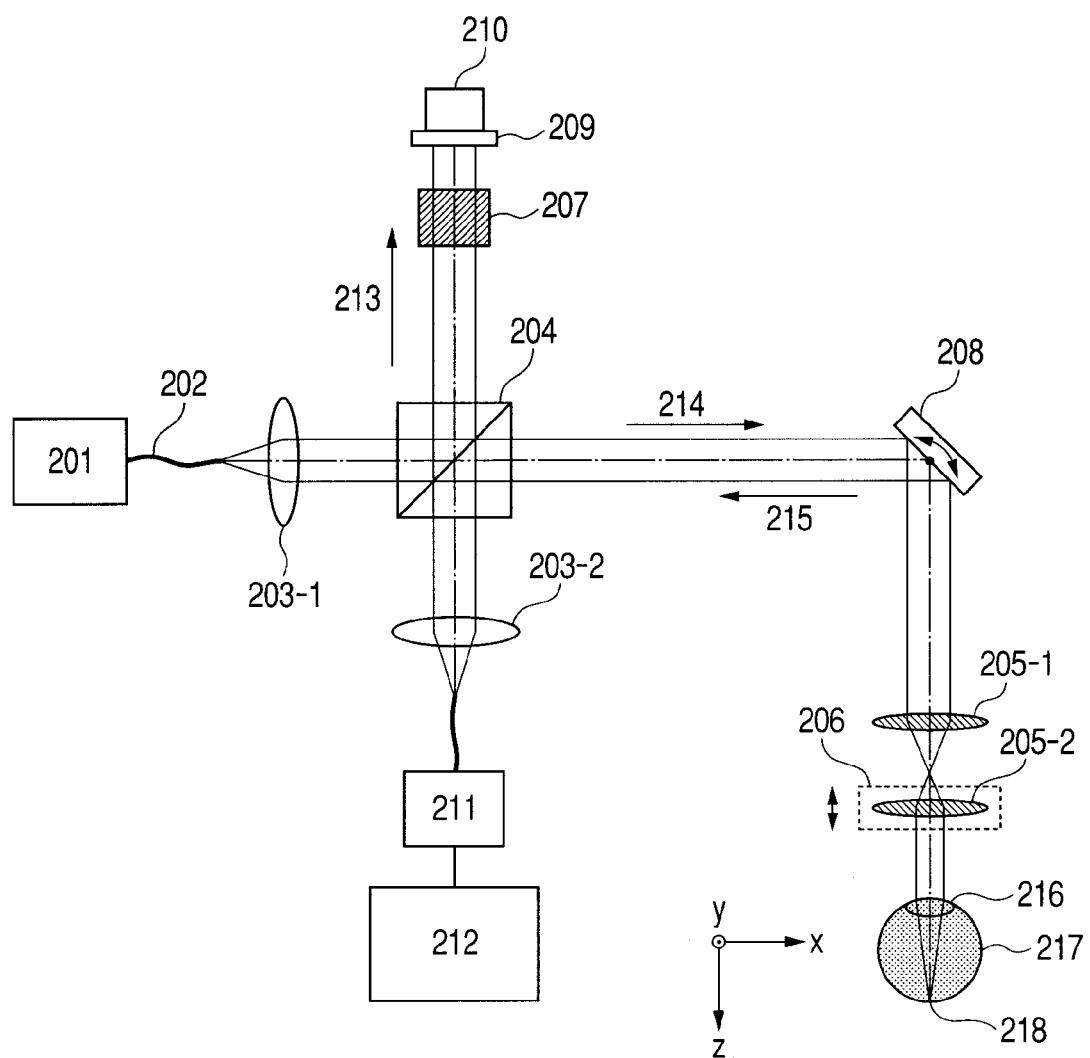
FIG. 2 is an explanatory diagram illustrating a Michelson OCT apparatus according to the first embodiment of the present invention.

An optical coherence tomographic imaging apparatus (hereinafter, also referred to as OCT apparatus) according to the first embodiment is described with reference to FIG. 2. FIG. 2 is a schematic diagram illustrating the imaging apparatus using the Michelson optical system (Michelson interferometer) according to this embodiment.

A light emitted from a light source 201 passes through a fiber 202 and a lens 203-1, and is split into a measurement light 214 and a reference light 213 by a beam splitter 204. The measurement light 214 passes through an XY scanner 208, an objective lens 205-1, and an objective lens 205-2, and enters an eye 217, which is an object. Then, the measurement light that has entered the eye passes through a cornea 216, and reaches a retina 218.

A return light 215 reflected and scattered on the retina 218 of the eye 217 returns by passing through the objective lens 205-2, the objective lens 205-1, the XY scanner 208, and the beam splitter 204 in the stated order. Further, the return light 215 is guided to a spectrometer 211 through a lens 203-2. The spectrometer 211 includes a lens, a grating, and an image-pickup device. Used as the image-pickup device is a line sensor of a charge coupled device (CCD) type or a complementary metal oxide semiconductor (CMOS) type. Signals obtained by the line sensor of the spectrometer 211 are sent to a computer 212 and stored in a memory. The stored signals are then subjected to processing described later.

On the other hand, the reference light 213 passes through a dispersion compensation glass 207, is reflected on a reference mirror 209, passes again through the dispersion compensation glass 207, and returns to the beam splitter 204. The dispersion compensation glass 207 is used for compensating for dispersion caused in the eye 217 and the objective lenses 205-1 and 205-2. The reference mirror 209 can adjust an optical path length of a reference light path by means of a mirror adjustment mechanism 210. These reference light 213 and return light 215 are combined by the beam splitter 204. Then, the combined light is guided to the spectrometer 211. Note that a portion on a measurement light path having an optical path length matching with that of the reference light path is referred to as a coherence gate. In a case where the retina 218 of the eye 217 is measured, the position of the reference mirror 209 is adjusted so that the coherence gate becomes close to the retina 218.

As the light source 201, a super luminescent diode (SLD), which is a typical low coherent light source, is used. As to the wavelength thereof, for example, the center wavelength is 840 nm and the bandwidth is 50 nm. Note that, the bandwidth is an important parameter because of its influence on the resolution of a tomographic image to be obtained in an optical axis direction. Besides, the type of the selected light source 201 is the SLD herein, and alternatively, amplified spontaneous emission (ASE) may be used therefor as long as the light source 201 emits low coherent light. Obviously, depending on contents of the object, another light source such as a halogen lamp may be used. Note that, the wavelength influences resolution of the tomographic image to be obtained in a lateral direction, and hence a short wavelength is desired when the resolution in the lateral direction is important.

The computer 212 performs arithmetic processing and control that are described later, and also controls the spectrometer 211, the XY scanner 208, the mirror adjustment mechanism 210, and a focus adjustment mechanism 206. Obviously, the computer 212 is also capable of data input, image processing, image display, and data storage.

Signal Processing Steps

The signal processing executed by the OCT apparatus illustrated in FIG. 2 is described with reference to FIG. 1. Among Steps A1 to A7, a combination step M1 is provided between Steps A2 and A3.

In Step A1, measurement is started. At this stage, the OCT apparatus is activated and an eye as an object is set for the measurement. Additionally, adjustment necessary for the measurement is performed by an operator so that the measurement can be started.

Figure 3A:
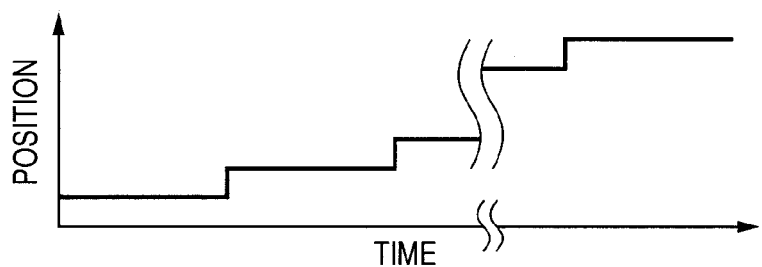
FIGS. 3A, 3B, 3C, and 3D are explanatory charts illustrating a relation between a position of a scanner with respect to a lapse of time and measurement timing thereof according to the first embodiment of the present invention.
Figure 3B:
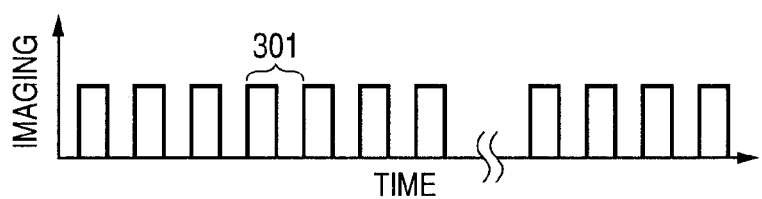

In Step A2, signals are acquired. In the following, a case of acquiring one two-dimensional tomographic image is described as an example. The XY scanner 208 is moved in an X direction of FIG. 2, which is perpendicular to the optical axis of the eye 217. FIGS. 3A to 3D are charts illustrating a relation between a position of the XY scanner 208 with respect to a lapse of time and imaging timing thereof. FIG. 3A illustrates a case where the XY scanner 208 moves in the X direction stepwise. The number of steps is, for example, 512. FIG. 3B illustrates measurement timings, and illustrates control of imaging performed three times at regular intervals in one step. Measurement intervals 301 are equal both for one step and between steps. Hence, the imaging is performed 1,536 (=512×3) times. Note that, as to data acquired per imaging, a one-dimensional array of 1,024 elements is obtained in a case of a line sensor having 1,024 pixels.

Therefore, since there are 1,536 lines, a two-dimensional array of 1,024×1,536 elements is obtained finally. Note that, the data of each line is stored as data of each column of the two-dimensional array.

Figure 3C:
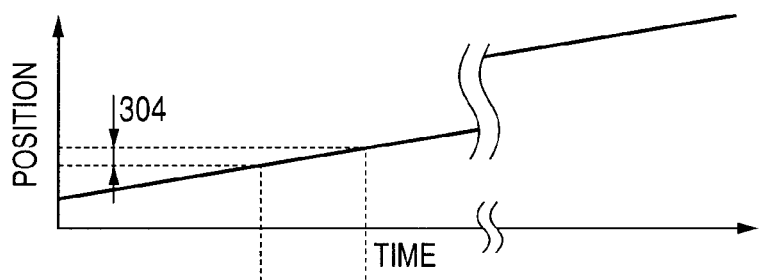
Figure 3D:
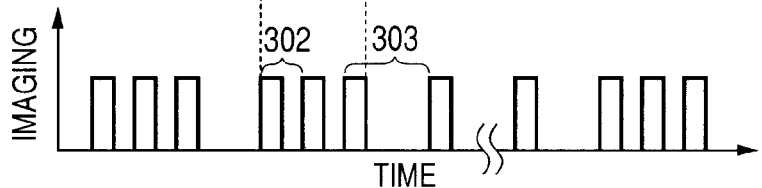

Note that, the XY scanner 208 may be moved in the X direction successively as illustrated in FIG. 3C. The successive movement reduces loads on the scanner and leads to smooth movement as compared with the above-mentioned case. The measurement intervals may be equal, and alternatively, such different intervals as a measurement interval 302 and a measurement interval 303 as illustrated in FIG. 3D may be provided. In this case, regular intervals are provided among three successive imaging operations for obtaining signals to be combined, while a different measurement interval is provided between adjacent two sets of the imaging operations. Obviously, the combination of the position control and the imaging timing is freely determined. The position control of the successive movement illustrated in FIG. 3C and the regular imaging timing illustrated in FIG. 3B may be employed in combination.

Note that, in a case of combining signals acquired through imaging performed while moving the XY scanner 208 in the X direction successively, when the moving distance is large, signal components may be rounded (data to be combined counteract each other so that original signal components may be lost). Therefore, it is desired that a moving distance 304 be equal to or smaller than a several-fold length of the lateral resolution of the OCT apparatus (generally determined based on a beam diameter of the measurement light on the object). Specifically, the moving distance 304 ranges from several micrometers to several hundred micrometers. Note that, in a case where a moving speed of the scanner is known, the predetermined distance may be converted into a time, and the time thus obtained may be set as a predetermined time. As long as the condition of the predetermined distance or the predetermined time is satisfied, the data may be acquired by rotating the XY scanner 208 like circle scanning instead of linear movement in the X or Y direction.

For example, in a case where imaging is performed by a 20-kHz line scanner for a range of 6 mm, the moving speed of the scanner at the time of scanning the object is 78 (=6/1,536× 20 k) mm/s. The moving distance when averaged for three lines is 12 (=78×(3/20 k)) μm. When the lateral resolution of the OCT apparatus is 20 μm, the moving distance falls within a range in which signal loss is less likely to occur even after the combination. Note that, the time necessary to acquire an image of 512 lines at 20 kHz is 25.6 (=512/20 k) msec. In a case of acquiring three images, at least 76.8 (=25.6×3) msec is necessary. The time necessary to acquire signals of three lines is 0.15 (=3/20 k) msec, in which the object does not move so widely.

In Step M1, the signals are combined. In this step, one-dimensional arrays of three adjacent spectra are averaged and a new one-dimensional array is created. Specifically, in the 1,024×1,536 two-dimensional array, one-dimensional arrays of 3j-th, (3j+1)th, and (3j+2)th columns (j is an integer ranging from 0 to 511) are averaged. As a result, a 1,024×512 two-dimensional array is obtained. Through the averaging, noise components may be removed.

As compared with a case of averaging performed in a process after Step A3, calculation may be performed with a smaller number of data, which leads to an effect of shortening the calculation time. Note that, the averaging may be weighted averaging, but the noise removal effect may vary when the weights are different. Note that, the number of lines to be averaged is not necessarily three in the case of the combination of control illustrated in FIGS. 3C and 3B, and may be an arbitrary integer that satisfies the condition of the lateral resolution described above. Further, data that is considered to have a measurement error may be removed.

In Step A3, wavelength-wavenumber conversion is performed. In general, data from the spectrometer 211 includes a wavelength and the intensity at the wavelength. Further, sampling is performed at regular intervals with regard to the wavelength. First, a function of intensity data with regard to the wavelength is created. Then, each wavelength is converted into a wavenumber, and a function of intensity data with regard to the wavenumber is created. The wavenumber is an inverse of the wavelength, and hence 1,024 wavenumbers are allocated at regular intervals. Then, intensity data corresponding to the wavenumbers is calculated. The calculation method to be employed is, for example, interpolation, which may be general linear interpolation or spline interpolation. In this case, a linear arithmetic operation is desired. As a result, a two-dimensional array of 1,024×512 elements including intensities at regular intervals with regard to the wavenumber is obtained.

In a case where the spectrometer 211 can perform sampling at regular intervals with regard to the wavenumber, this step may obviously be omitted as long as an error due to the wavelength-wavenumber conversion is negligible.

In Step A4, Fourier transform is performed. In this step, the intensity values arranged at regular intervals with regard to the wavenumber are subjected to discrete Fourier transform for each column. As a result, a 1,024×512 two-dimensional array of complex numbers is obtained. Note that, an m-th row and a (1,024-m)th row of each column have the same intensity value because of the characteristics of the Fourier transform. Therefore, 0th to 511th rows are extracted and a 512×512 two-dimensional array of complex numbers is obtained.

In Step A5, the complex number data is converted into real number data. It is not the linear arithmetic operation that is used for converting the complex number into a real number. Therefore, averaging before Step A5 is fundamentally different from averaging after Step A5. The difference is described in a second embodiment.

In Step A6, a tomographic image is obtained. In this step, a range is further adjusted in the 512×512 two-dimensional array.

The range to be adjusted is, for example, the ratio of a longitudinal length to a lateral length. To adjust the range, the number of pixels is increased and decreased through interpolation. Further, contrast is adjusted. The adjustment of the contrast refers to general correction of the γ value used for image processing. As a result, an image suitable for doctor's diagnosis is obtained. Then, the obtained tomographic image is displayed on a display screen of the computer 212.

In Step A7, the process ends. The process starting from the measurement using the OCT apparatus to the image display has been described above, and alternatively, for example, the above-mentioned process may be applied to data of multiple frames acquired via a network, to thereby obtain an image with reduced noise from a single tomographic image.

According to this embodiment, a high-quality image can be obtained by combining signals acquired within a predetermined time.

Second Embodiment

Next, a second embodiment of the present invention is described. In this embodiment, an imaging apparatus using a Mach-Zehnder interferometer is employed for generating a tomographic image, but the imaging apparatus employable for the present invention is not limited thereto. Further, signal processing of this embodiment is characterized in signal combination performed after Fourier transform.

Mach-Zehnder Interferometer

Figure 4:
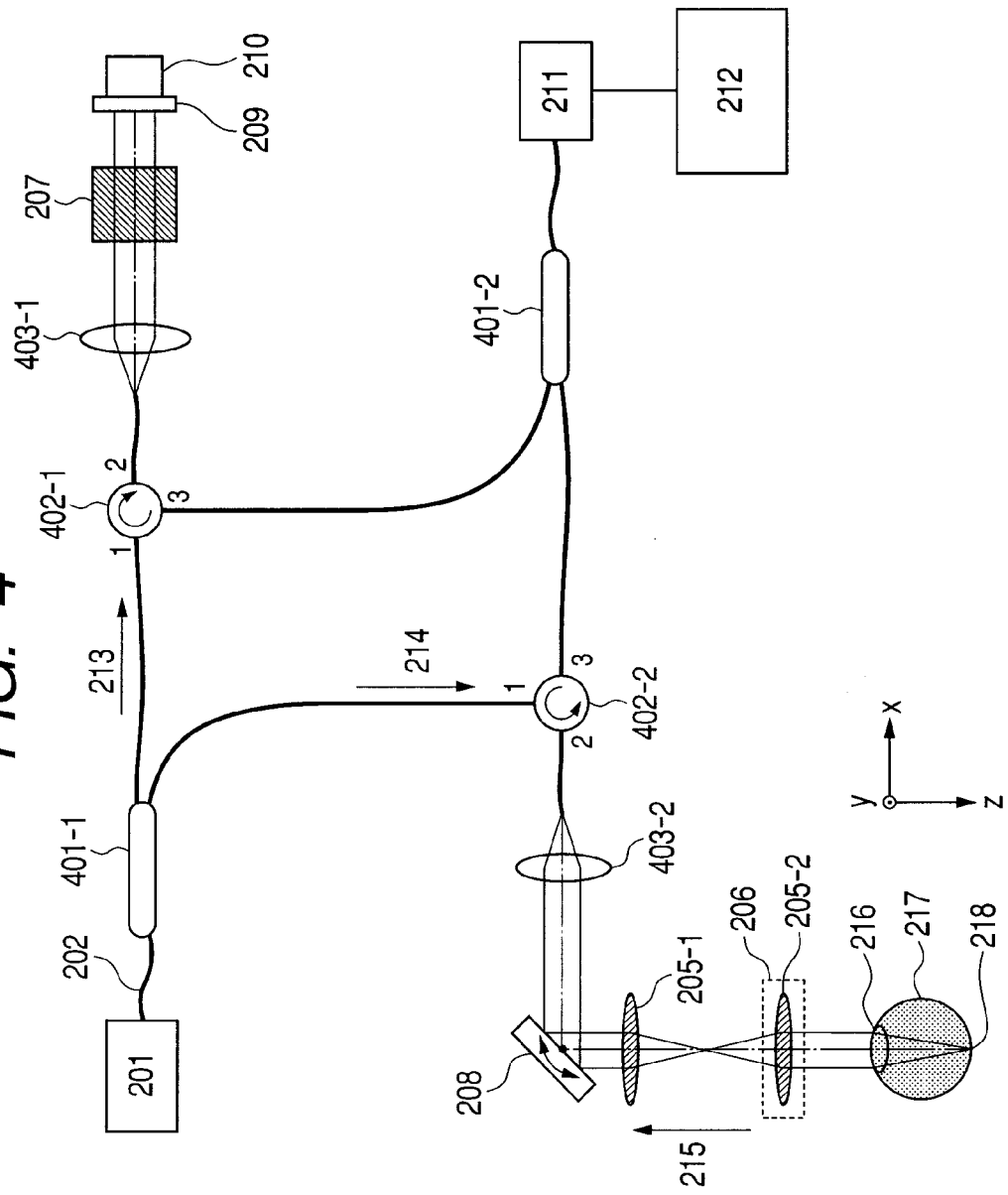
FIG. 4 is an explanatory diagram illustrating a Mach-Zehnder OCT apparatus according to a second embodiment of the present invention.

An optical coherence tomographic imaging apparatus according to the second embodiment is described with reference to FIG. 4. FIG. 4 is a schematic diagram illustrating the imaging apparatus using the Mach-Zehnder optical system according to this embodiment. Differences from the first embodiment are described below.

A light emitted from the light source 201 passes through a fiber coupler 401-1, and is split into a measurement light 214 and the reference light 213.

The measurement light enters a port 1 of a circulator 402-2, exits from a port 2 thereof, and reaches a lens 403-2. Further, the measurement light passes through a XY scanner 208, an objective lens 205-1, an objective lens 205-2, and a cornea 216 of an eye 217, and reaches a retina 218. The return light 215 scattered and reflected on the retina returns by passing through the objective lens 205-2, the objective lens 205-1, the XY scanner 208, and the lens 403-2, enters the port 2 of the circulator 402-2, exits from a port 3 thereof, and reaches a fiber coupler 401-2.

On the other hand, the reference light 213 enters a port 1 of a circulator 402-1, exits from a port 2 thereof, passes through a lens 403-1 and a dispersion compensation glass 207, and is reflected on a reference mirror 209. The reflected reference light 213 returns to the port 2 of the circulator 402-1 by passing through the dispersion compensation glass 207 and the lens 403-1, exits from a port 3 of the circulator 402-1, and reaches the fiber coupler 401-2. The reference mirror 209 can adjust the optical path length by means of the mirror adjustment mechanism 210. The reference light 213 and the return light 215 are combined by the fiber coupler 401-2, and the combined light is guided to the spectrometer.

Signal Processing Steps

The signal processing executed by the OCT apparatus illustrated in FIG. 4 is described with reference to FIGS. 5A and 5B. FIG. 5A illustrates a case where, among Steps A1 to A7, a combination step M2 is provided between Steps A4 and A5. FIG. 5B illustrates a case where a combination step M3 is provided between Steps A5 and A6.

The difference between the two cases is now described. First, in the case of Step M2, complex number data obtained in Step A4 is combined, and the resultant complex number data is passed to Step A5. In the combination step M2, simple averaging or weighted averaging is performed on the complex number data. On the other hand, in the case of Step M3, real number data calculated in Step A5 is combined, and the resultant real number data is passed to Step A6. In the combination step M3, simple averaging or weighted averaging is performed on the real number data.

The combination based on the complex number in Step M2 is fundamentally different from the combination based on the real number in Step M3. The difference is described with reference to the following mathematical expressions. In the following, an element 1 and an element 2 of the complex numbers are represented by Expression 1-1 and Expression 1-2 using an imaginary unit i, respectively.

$$a_0 + b_0 i = r_0 e(i\varphi_0) \quad \text{Expression 1-1}$$

$$a_1 + b_1 i = r_1 e(i\varphi_1) \quad \text{Expression 1-2}$$

When the complex numbers are added together and then the resultant complex number is converted into a real number, data represented by Expression 2 is obtained.

$$\sqrt{(a_0+a_1)^2 + (b_0+b_1)^2} \quad \text{Expression 2}$$

When the complex numbers are converted into real numbers and then the resultant real numbers are added together, data represented by Expression 3 is obtained.

$$\sqrt{a_0^2+b_0^2} + \sqrt{a_1^2+b_1^2} \quad \text{Expression 3}$$

When Expression 2 and Expression 3 are squared and then common parts are subtracted, a relation of Expression 4 is established (proof is easily obtained by further squaring both sides).

$$a_0 a_1 + b_0 b_1 \leq \sqrt{a_0^2+b_0^2}\sqrt{a_1^2+b_1^2} \quad \text{Expression 4}$$

In other words, the value of Expression 2 is equal to or smaller than the value of Expression 3. This fact is important in the noise removal method. Specifically, in a case of random noise, a plus component and a minus component exist. When the two components are added together in the state of the complex number, those components are canceled. Therefore, in theory, when the steps of FIGS. 5A and 5B are compared with each other, noise is further reduced through the steps of FIG. 5A. In contrast, when real numbers are obtained and then added together, the cancellation effect is limited. Note that, in the first embodiment, the linear arithmetic operation is performed until the Fourier transform, and hence the same effect may be obtained as in the case of adding the components together in the state of the complex number. Note that, the simple averaging is more desired than the weighted averaging because the noise is equivalent.

Table 1 shows comparison in signal-to-noise ratio (SNR) between the processing involving the steps of FIG. 1 and the processing involving the steps of FIG. 5B. The unit is decibel. As the position control for the scanner, the case of FIG. 3C where the position of the scanner is shifted successively is applied. As the imaging timing, the case of FIG. 3B where sampling is performed at regular intervals is applied. The imaging object is centered on a macula of a normal eye, and a retina is measured in the range of approximately 6 mm. The number of lines is 2,048. The same original data is used and values of the SNR are obtained through each processing in cases where: (1) every four lines are extracted from 2,048 lines, to thereby create a tomographic image of 512 lines, which is not subjected to combination; (2) every two lines are extracted from 2,048 lines to obtain 1,024 lines, and further, two adjacent lines are combined, to thereby create a tomographic image of 512 lines; and (3) four lines of 2,048 lines are combined, to thereby create a tomographic image of 512 lines. In the case of combining lines before the complex numbers are converted into real numbers, the SNR is improved as the number of combined lines becomes larger. On the other hand, in the case of combining lines after the complex numbers are converted into real numbers, the SNR is almost constant. When the case where averaging processing is not performed is compared with the case where averaging processing is performed after real numbers are obtained, a smoother image is obtained in the latter case. Note that, the SNR used in this comparison refers to a ratio of a maximum value of each pixel to a minimum value of root mean squares (RMSs) of noise of the rows thereof.

TABLE 1

Comparison in SNR

|  | Steps of FIG. 1 | Steps of FIG. 5B |
| --- | --- | --- |
| 512 (no averaging) | 40.22 | 40.22 |
| 1,024 (two-line averaging) | 42.84 | 40.27 |
| 2,048 (four-line averaging) | 45.74 | 40.35 |

According to this embodiment, a high-quality image can be obtained by combining signals acquired within a predetermined time.

Third Embodiment

Next, a third embodiment of the present invention is described. In signal processing of this embodiment, phase adjustment is performed after the Fourier transform, and then signals are combined.

Signal Processing Steps

Figure 6:
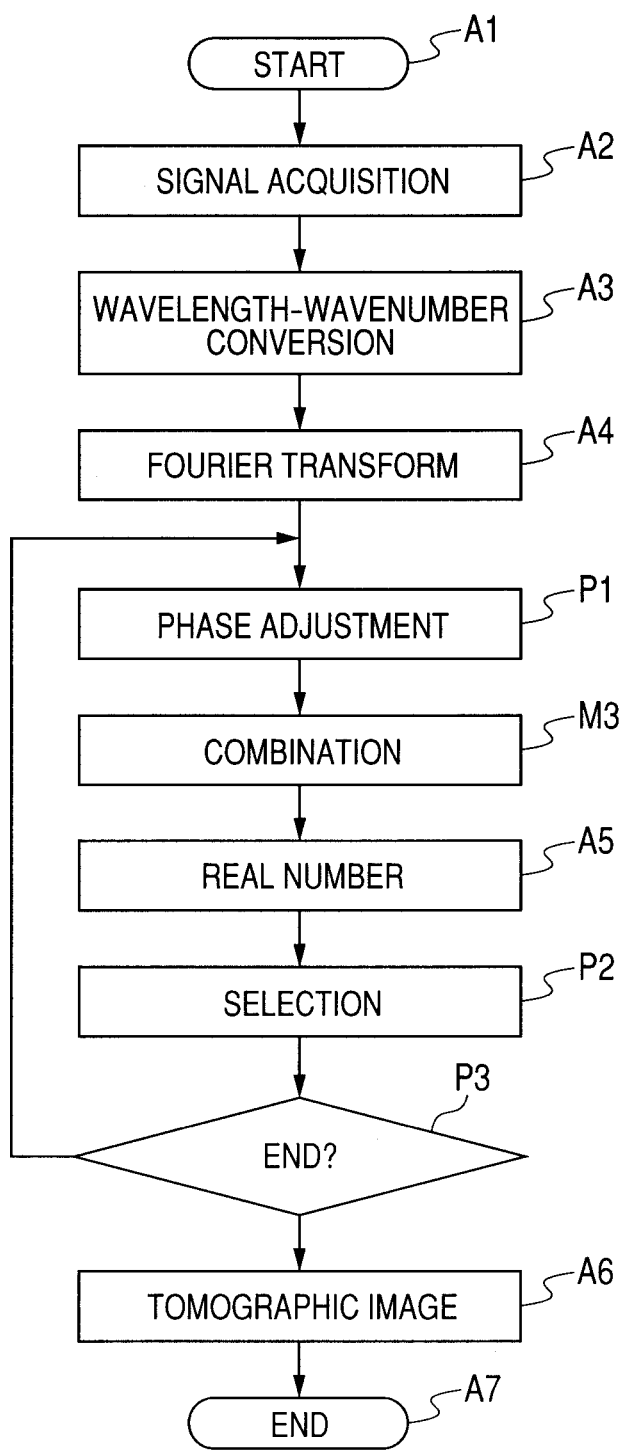
FIG. 6 is an explanatory diagram illustrating signal processing steps according to a third embodiment of the present invention.

The signal processing of this embodiment is described with reference to FIG. 6. A phase adjustment step and a combination step are provided between Steps A4 and A5. Differences from the second embodiment are described below.

In Step P1, complex number data are subjected to phase adjustment. In this step, phases of arrays of three adjacent lines are adjusted. First, the data are converted into sets of polar coordinates. An amplitude component and a phase component can be obtained from the polar coordinates. With the first line of the three lines set as the 3j-th column (j is an integer ranging from 0 to 511), the phase of the one-dimensional array of the (3j+1)th column is adjusted with reference to the phase of the 3j-th column (or the phase of the (3j+2)th column is adjusted with reference to a result of combination of the 3j-th column and the (3j+1)th column). First, new arrays are created by changing a phase component of the array of the (3j+1)th column. When the phase component is changed by, for example, 10 degrees from 0 degrees to 350 degrees, 36 different one-dimensional arrays may be obtained.

In Step M3, combination is performed. The one-dimensional array of the 3j-th column is combined with the 36 different one-dimensional arrays, respectively. In this step, simple averaging is performed, to thereby newly obtain 36 different arrays.

In Step A5, real number data are obtained. There are obtained 36 different arrays of real numbers from the 36 different arrays obtained through the combination.

In Step P2, selection is performed. From among the 36 different arrays obtained through the combination, an array in which the signal is maximum is selected. While the noise removal effect is mainly obtained in the first and second embodiments, the signal can be maximized in this embodiment. Further, in the case of random noise, the noise is random even with the phase adjustment, and hence the noise removal effect is still obtained.

In Step P3, it is determined whether or not the combination is finished. Specifically, the three lines in the 3j-th column to the (3j+2)th column are combined, to thereby create a new 3j-th column. It is determined whether or not such combination is finished for all j's. When the combination is finished, the processing proceeds to Step A6. When the combination is not finished, the processing returns to Step P1.

According to this embodiment, a high-quality image can be obtained by using data of adjacent lines.

The above-mentioned optical tomographic image generation methods according to the present invention may be executed by using a computer with the procedure for performing the respective steps implemented by a computer program.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium). In such a case, the system or apparatus, and the recording medium where the program is stored, are included as being within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-244696, filed Oct. 23, 2009, which is hereby incorporated by reference herein in its entirety.

What is claimed is:

1. An optical tomographic image generation method of generating at least one two-dimensional tomographic image of an eye based on a plurality of intensity signals of a plurality of lines of a combined light of (a) a return light from the eye to which a measurement light has been applied and (b) a reference light that corresponds to the measurement light, the optical tomographic image generation method comprising the steps of:
   acquiring the plurality of intensity signals using a scanning unit which is arranged so as to move a measurement light that is applied to a retina of the eye through a cornea of the eye on the retina in a direction crossing an optical axis of an optical path of the measurement light;
   performing Fourier transformations on the plurality of intensity signals;
   averaging, in a state of complex numbers, the plurality of intensity signals after performing Fourier transformations on the plurality of intensity signals;
   converting the averaged plurality of intensity signals into real number data; and
   generating the at least one two-dimensional tomographic image of the eye based on the real number data,
   wherein the plurality of intensity signals are acquired after a coherence gate is adjusted to move toward the retina of the eye within a predetermined time when acquiring one two-dimensional tomographic image of the eye, and
   wherein the predetermined time is acquired based on at least (a) a scanning speed of the measurement light scanning the retina by using the scanning unit and (b) a lateral resolution of the measurement light scanning the retina by using the scanning unit used for acquiring the plurality of intensity signals.

2. The optical tomographic image generation method according to claim 1, wherein the step of averaging is a step of weighted averaging the plurality of intensity signals.

3. The optical tomographic image generation method according to claim 1, wherein the step of averaging is a step of adjusting phases of the plurality of intensity signals after performing Fourier transformations on the plurality of intensity signals.

4. The optical tomographic image generation method according to claim 3, wherein the step of adjusting phases is performed so that an average of the plurality of intensity signals is maximized.

5. The optical tomographic image generation method according to claim 1, further comprising a step of scanning the measurement light on the eye,
   wherein the scanning is performed stepwise.

6. The optical tomographic image generation method according to claim 1, further comprising the steps of:
   adjusting a ratio of a longitudinal length to a lateral length of the two-dimensional tomographic image of the eye acquired by the step of averaging; and
   displaying, on a display unit, the two-dimensional tomographic image of the eye acquired by the step of adjusting.

7. An optical tomographic image generation apparatus that generates at least one two-dimensional tomographic image of an eye based on a plurality of intensity signals of a plurality of lines of a combined light of (a) a return light from the eye to which a measurement light has been applied and (b) a reference light that corresponds to the measurement light, the optical tomographic image generation apparatus comprising:
   an acquiring unit that acquires the plurality of intensity signals using a scanning unit which is arranged so as to move the measurement light that is applied to the retina of the eye through the cornea of the eye on the retina in a direction crossing an optical axis of an optical path of the measurement light;
   a performing unit that performs Fourier transformations on the plurality of intensity signals;
   an averaging unit that averages, in a state of complex numbers, the plurality of intensity signals after performing Fourier transformations on the plurality of intensity signals;
   a converting unit that converts the averaged plurality of intensity signals into real number data; and
   a generating unit that generates the at least one two-dimensional tomographic image of the eye based on the real number data,
   wherein the plurality of intensity signals are acquired after a coherence gate is adjusted to move toward the retina of the eye within a predetermined time when acquiring one two-dimensional tomographic image of the eye, and wherein the predetermined time is acquired based on at least (a) a scanning speed of the measurement light scanning the retina by using the scanning unit and (b) a lateral resolution of the measurement light scanning the retina by using the scanning unit used for acquiring the plurality of intensity signals.

8. The optical tomographic image generation apparatus according to claim 7, wherein the scanning is performed stepwise.

9. The optical tomographic image generation apparatus according to claim 7, further comprising a control unit that controls an imaging timing,
wherein the imaging timing is a combination of a plurality of intervals.

10. The optical tomographic image generation apparatus according to claim 7, wherein the averaging is weighted averaging of the plurality of intensity signals.

11. The optical tomographic image generation apparatus according to claim 7, further comprising:
an adjusting unit that adjusts a ratio of a longitudinal length to a lateral length of the two-dimensional tomographic image of the eye acquired by the averaging unit; and
a displaying unit that displays, on a display unit, the two-dimensional tomographic image of the eye acquired by the adjusting unit.

12. A non-transitory computer-readable media storing computer-executable instructions, in order to acquire at least one two-dimensional tomographic image of an eye based on a plurality of intensity signals of a plurality of lines of a combined light of (a) a return light from the eye to which a measurement light has been applied and (b) a reference light that corresponds to the measurement light, for performing a method comprising the steps of:
acquiring the plurality of intensity signals using a scanning unit which is arranged so as to move a measurement light that is applied to a retina of the eye through a cornea of the eye on the retina in a direction crossing an optical axis of an optical path of the measurement light;
performing Fourier transformations on the plurality of intensity signals;
averaging, in a state of complex numbers, the plurality of intensity signals after performing Fourier transformations on the plurality of intensity signals;
converting the averaged plurality of intensity signals into real number data; and
generating the at least one two-dimensional tomographic image of the eye based on the real number data,
wherein the plurality of intensity signals are acquired after a coherence gate is adjusted to move toward the retina of the eye within a predetermined time when acquiring one two-dimensional tomographic image of the eye, and
wherein the predetermined time is acquired based on at least (a) a scanning speed of the measurement light scanning the retina by using the scanning unit and (b) a lateral resolution of the measurement light scanning the retina by using the scanning unit used for acquiring the plurality of intensity signals.

13. An optical tomographic image generation method of generating at least one two-dimensional tomographic image of an eye based on a plurality of intensity signals of a plurality of lines of a combined light of (a) a return light from the eye to which a measurement light has been applied and (b) a reference light that corresponds to the measurement light, the optical tomographic image generation method comprising the steps of:
performing Fourier transformations on the plurality of intensity signals;
averaging, after performing Fourier transformations on the plurality of intensity signals, the plurality of intensity signals in a state of complex numbers within a predetermined time in a scanning time of the measurement light applied to the eye when acquiring one two-dimensional tomographic image of the eye;
converting the averaged plurality of intensity signals into real number data; and
generating one two-dimensional tomographic image of the eye in the scanning time based on the real number data.

14. An optical tomographic image generation apparatus for generating at least one two-dimensional tomographic image of an eye based on a plurality of intensity signals of a plurality of lines of a combined light of (a) a return light from the eye to which a measurement light has been applied and (b) a reference light that corresponds to the measurement light, the optical tomographic image generation apparatus comprising:
a performing unit that performs Fourier transformations on the plurality of intensity signals;
an averaging unit that averages, after performing Fourier transformations on the plurality of intensity signals, the plurality of intensity signals in a state of complex numbers within a predetermined time in a scanning time of the measurement light scanning the eye when acquiring one two-dimensional tomographic image of the eye;
a converting unit that converts the averaged plurality of intensity signals into real number data; and
a generating unit that generates the at least one two-dimensional tomographic image of the eye based on the real number data.

15. An optical tomographic image generation method of generating at least one two-dimensional tomographic image of an eye based on a plurality of intensity signals of a plurality of lines of a combined light of (a) a return light from the eye to which a measurement light has been applied and (b) a reference light that corresponds to the measurement light, the optical tomographic image generation method comprising the steps of:
performing Fourier transformations on the plurality of intensity signals; and
averaging the plurality of intensity signals in a state of complex numbers after performing Fourier transformations on the plurality of intensity signals;
converting the averaged plurality of intensity signals into real number data; and
generating the at least one two-dimensional tomographic image of the eye based on the real number data.

16. An optical tomographic image generation apparatus for generating at least one two-dimensional tomographic image of an eye based on a plurality of intensity signals of a plurality of lines of a combined light of (a) a return light from the eye to which a measurement light has been applied and (b) a reference light that corresponds to the measurement light, the optical tomographic image generation apparatus comprising:
a performing unit that performs Fourier transformations on the plurality of intensity signals;
an averaging unit that averages the plurality of intensity signals in a state of complex numbers after performing Fourier transformations on the plurality of intensity signals;
a converting unit that converts the averaged plurality of intensity signals into real number data; and
a generating unit that generates the at least one two-dimensional tomographic image of the eye based on the real number data.

17. An optical tomographic image generation apparatus for generating at least one two-dimensional tomographic image of an eye based on a plurality of intensity signals of a plurality of lines of a combined light of (a) a return light from the eye to which a measurement light has been applied through a scanning unit, and (b) a reference light that corresponds to the measurement light, the optical tomographic generation apparatus comprising:
- a performing unit that performs Fourier transformations on the plurality of intensity signals;
- an averaging unit that averages, after performing Fourier transformations on the plurality of intensity signals, the plurality of intensity signals in a state of complex numbers in a range based on a lateral resolution of the measurement light scanning the eye when acquiring one two-dimensional tomographic image of the eye by scanning the eye with the measurement light by the scanning unit;
- a converting unit that converts the averaged plurality of intensity signals into real number data; and
- a generating unit that generates the at least one two-dimensional tomographic image of the eye based on the real number data.

18. The optical tomographic image generation apparatus according to claim 17, wherein a scanning distance of the scanning unit is equal to or smaller than a several-fold length of the lateral resolution.

19. The optical tomographic image generation apparatus according to claim 17, wherein the lateral resolution corresponds to a size of the measurement light on the eye.

20. The optical tomographic image generation apparatus according to claim 17, further comprising:
- a determining unit that determines a scanning speed of the measurement light based on the lateral resolution; and
- a control unit that controls the scanning unit based on the determined scanning speed.

21. The optical tomographic image generation apparatus according to claim 17, wherein the averaging unit weighted averages the plurality of intensity signals.

22. The optical tomographic image generation apparatus according to claim 17, further comprising:
- an adjusting unit that adjusts a ratio of a longitudinal length to a lateral length of the two-dimensional tomographic image of the eye acquired by the averaging unit; and
- a displaying unit that displays, on a display unit, the two-dimensional tomographic image of the eye acquired by the adjusting unit.

23. An optical tomographic image generation method of generating at least one two-dimensional tomographic image of an eye based on a plurality of intensity signals of a plurality of lines of a combined light of (a) a return light from the eye to which a measurement light has been applied through a scanning unit and (b) a reference light that corresponds to the measurement light, the optical tomographic generation method comprising the step of:
- performing Fourier transformations on the plurality of intensity signals;
- averaging, after performing Fourier transformations on the plurality of intensity signals, the plurality of intensity signals of the plurality of lines in a state of complex numbers in a range based on a lateral resolution of the measurement light scanning the eye when acquiring one two-dimensional tomographic image of the eye by scanning the eye with the measurement light by the scanning unit;
- converting the averaged plurality of intensity signals into real number data; and
- generating the at least one two dimensional tomographic image of the eye based on the real number data.

24. The optical tomographic image generation method according to claim 23, wherein a scanning distance of the scanning unit is equal to or smaller than a several-fold length of the lateral resolution.

25. The optical tomographic image generation method according to claim 23, wherein the lateral resolution corresponds to a size of the measurement light on the eye.

26. The optical tomographic image generation method according to claim 23, further comprising the steps of:
- determining a scanning speed of the measurement light based on the lateral resolution; and
- controlling the scanning unit based on the determined scanning speed.

27. The optical tomographic image generation method according to claim 23, the step of averaging is a step of weighted averaging the new intensity signals.

28. The optical tomographic image generation method according to claim 23, further comprising the steps of:
- adjusting a ratio of a longitudinal length to a lateral length of the two-dimensional tomographic image of the eye acquired by the step of averaging; and
- displaying, on a display unit, the two-dimensional tomographic image of the eye acquired by the step of adjusting.

29. A computer program stored on a non-transitory computer-readable medium that causes a computer to execute the optical tomographic image generation method according to claim 23.

* * * * *